(12) United States Patent
Wachs et al.

(10) Patent No.: US 6,552,233 B2
(45) Date of Patent: Apr. 22, 2003

(54) VANADIA-TITANIA/METAL-MOLYBDATE DUAL CATALYST BED SYSTEM AND PROCESS USING THE SAME FOR METHANOL OXIDATION TO FORMALDEHYDE

(75) Inventors: Israel E. Wachs, Bridgewater, NJ (US); Ray P. Bourne, Eugene, OR (US)

(73) Assignees: Lehigh University, Bethlehem, PA (US); Georgia-Pacific Resings, Inc., Atlanta, GA (US)

( * ) Notice: Subject to any disclaimer, the term of this patent is extended or adjusted under 35 U.S.C. 154(b) by 19 days.

(21) Appl. No.: 09/950,833

(22) Filed: Sep. 13, 2001

(65) Prior Publication Data

US 2002/0055659 A1 May 9, 2002

Related U.S. Application Data

(60) Provisional application No. 60/232,511, filed on Sep. 14, 2000.

(51) Int. Cl.[7] ............................................... C07C 45/29
(52) U.S. Cl. ...................... 568/471; 568/472; 568/474
(58) Field of Search ............................... 568/471, 474, 568/472

(56) References Cited

U.S. PATENT DOCUMENTS

| | | |
|---|---|---|
| 2,065,394 A | 12/1936 | Punnett |
| 3,716,497 A | 2/1973 | Courty |
| 3,846,341 A | 11/1974 | Courty |
| 3,975,302 A | 8/1976 | Courty et al. |
| 3,978,136 A | 8/1976 | Friedrich et al. |
| 3,983,073 A | 9/1976 | Trifiro et al. |
| 3,987,107 A | 10/1976 | McClellan et al. |
| 3,994,977 A | 11/1976 | Aicher et al. |
| 4,024,074 A | 5/1977 | Cairati et al. |
| 4,080,383 A | 3/1978 | Diem et al. |
| 4,181,629 A | 1/1980 | Cairati et al. |
| 4,343,954 A | 8/1982 | Hoene |
| 4,421,938 A | 12/1983 | Windawi |
| 4,584,412 A | 4/1986 | Aicher et al. |
| 4,829,042 A | 5/1989 | Cavalli et al. |
| 5,217,936 A | 6/1993 | Sarup et al. |
| 6,245,708 B1 | 6/2001 | Wachs et al. |

FOREIGN PATENT DOCUMENTS

| | | |
|---|---|---|
| EP | 0199 359 | 10/1986 |
| GB | 1 463 174 | 2/1977 |
| WO | WO 98/23360 | 6/1998 |
| WO | WO 99/52629 | 10/1999 |
| WO | WO 99/52630 | 10/1999 |

OTHER PUBLICATIONS

"Fluidized bed improves formaldehyde process", C&EN, pp. 37–38, Nov. 13, 1980.

POPOV et al., "Study of an Iron–Molybdenum Oxide Catalyst for the Oxidation of Methanol to Formaldehyde", Institute of Catalysis, Siberian Branch of the Academy of Sciences of the USSR, Novosibinsk, Transcript from Kiretika & Kataliz, vol. 17, No. 2, pp. 371–377, Mar.–Apr. 1976.

E.M. McCarron III et al., "Oxy–Methoxy Compounds of Molybdenum (VI) and their relationship to the Selective Oxidation of Methanol Over Molybdate Catalysts, Polyhedron", vol. 5, No. 1/2, pp. 129–139 (1986).

L. Cairati et al, "Oxidation of Methanol in a Fluidized Bed Fe2 O3–MoO3 Supported Silica", Chemistry and Uses of Molybdenum, Proceedings of the Fourth International Conference, Climax Molybdenum Company, H.F. Baum and P.C.H. Mitchell, Editors, pp. 402–405, Aug. 9–13, 1982.

G. Deo, et al. "Physical and Chemical Characterization of Surface Vanadium Oxide Supported on Titania: Influence of the Titania Phase (anatase, rutile, brookite and B)" Applied Catalysis A: General, 91 (1992) 27–42, Elsevier Science Publishers B.V. Amsterdam.

Jih–Mirn Jehng, et al., "Surface Chemistry of Silica–Titania–supported Chromium Oxide Catalysts", J. Chem. Soc. Faraday Trans., 1995, 91(5), 953–961.

G. Deo, et al., "Effect of Additives on the Structure and Reactivity of the Surface Vanadium Oxide Phase in $V_2O_5$/$TiO_2$ Catalysts", Journal of Catalysts 146, 335–345,(1994).

M. Banares, et al., "Molybdena on Silica Catalysts: Role of Preparation Methods on the Structure–Selectivity Properties for the Oxidation of Methanol", Journal of Catalysis 150, 407–420 (1994).

Jih–Mirn Jehng, et al., "Surface Modified Niobium Oxide Catalyst: Synthesis, Characterization, and Catalysis", Applied Catalysis A: General 83 (1992) 179–200, Elsevier Science Publishers B.V. Amsterdam.

(List continued on next page.)

*Primary Examiner*—Johann Richter
*Assistant Examiner*—Sikarl A. Witherspoon (57) ABSTRACT

A process and a catalyst reaction zone comprising one or more fixed bed reactors for oxidizing methanol in a reactant gas feed stream to formaldehyde. According to one embodiment, the process comprises introducing the reactant gas feed stream into an upstream region containing a vanadia-titania first catalyst (substantially free of a volatile $MoO_3$ species) under oxidizing conditions to form a partially oxidized reactant gas feed stream which is then introduced under oxidizing conditions into a downstream region containing a metal molybdate second catalyst to further oxidize any residual methanol contained therein. According to another embodiment, a fixed bed reactor comprising an upstream region and a downstream region containing the aforementioned vanadia-titania and metal molybdate catalysts, respectively, is utilized to implement the inventive process to yield a product gas stream containing formaldehyde preferably at a conversion of 85% or more and a selectivity of 90% or more.

24 Claims, 2 Drawing Sheets

OTHER PUBLICATIONS

Jih–Mirn Jehng, et al., "Molecular Design of Supported Niobium Oxide Catalysts", Catalysts Today, 16 (1993) 417–426, Elsevier Science Publishers B.V. Amsterdam.

D.K. Kim, et al., Surface Rhenium Oxide–Support Interaction for Supported $Re_2O_7$ Catalysts, Journal of Catalysts 141 (419–429) (1993).

Jih–Mim Jehng, et al., "The Molecular Structures and Reactivity of $V_2O_5/TiO_2/SiO_2$ Catalysis", Catalysis Letters 13(1992) 9–20.

D.S. Kim, et al., "Molecular Structures and Reactivity of Supported Molybdenum Oxide Catalysts", Journal of Catalysis 146, 268–277 (1994).

G. Deo, et al., "Reactivity of Supported Vanadium Oxide Catalysts: The Partial Oxidation of Methanol", Journal of Catalysis 146, 323–334 (1994).

VANADIA-TITANIA/METAL-MOLYBDATE DUAL CATALYST BED SYSTEM AND PROCESS USING THE SAME FOR METHANOL OXIDATION TO FORMALDEHYDE

This application claims the benefit under 35 U.S.C. 119(e)(1) of prior filed provisional application No. 60/232,511 filed Sep. 14, 2000.

BACKGROUND OF THE INVENTION

1. Field of the Invention

The invention relates to a catalytic reactor bed arrangement comprising, in a specified distribution, a plurality of catalysts in one or more fixed bed reactors and a process using the same for oxidation of methanol to formaldehyde. More particularly, the invention relates to (1) a catalytic reaction zone (e.g., one or more catalytic reactor beds) comprising, in a specified distribution, a first catalyst of vanadia-titania and a metal molybdate second catalyst, provided in one or more fixed bed reactors, and (2) a process using the same for oxidizing methanol or methanol containing gas streams (i.e., paper pulp mill waste streams) to formaldehyde ($CH_2O$).

2. Description of the Related Art

The formation of formaldehyde involves the dehydrogenation and oxidation of methanol. One approach for converting methanol to formaldehyde involves oxidizing methanol over a silver catalyst. See, for example, U.S. Pat. Nos. 4,080,383; 3,994,977; 3,987,107; 4,584,412; 4,343,954 and 4,343,954. Typically, methanol oxidation to formaldehyde over a silver catalyst is carried out in an oxygen lean environment. One problem associated with silver catalyzed methanol oxidation is methanol leakage, i.e., high amounts of unconverted methanol.

Accordingly, improved processes for oxidizing methanol to formaldehyde have been developed. These processes use a methanol/air mixture (e.g., a reactant gas feed stream of methanol, excess air and an inert carrier gas) introduced over an iron-molybdate/molybdenum trioxide catalyst. See, for example, 3,983,073 (conversion of methanol to formaldehyde using $Fe_2(MoO_4)_3$ and $MoO_3$ having a molar ratio of Mo/Fe from 1.5 to 1.7 and a degree of crystallinity of at least 90%); 3,978,136 (process for the conversion of methanol to formaldehyde with a $MoO_3/Fe_2O_3/TiO_2$ catalyst wherein the $MoO_3$:$Fe_2O_3$ weight ratio is between 1:1 to 10:1 and $TiO_2$ is present between 1 to 90 weight % of total oxides); 3,975,302 (a supported iron oxide and molybdenum troxide catalyst wherein the atomic ratio of Mo/Fe is from 1.5 to 5); 3,846,341 (a shaped and optionally supported iron molybdate type catalyst having high mechanical strength made by reacting ammonium molybdate and ferric molybdate); 3,716,497 (an optionally shaped iron molybdate type catalyst made by admixing with $NH_4^+A^-$); 4,829,042 (high mechanical strength catalyst of $Fe_2(MoO_4)_3$ and $MoO_3$ together with non-sintered $Fe_2O_3$); 4,024,074 (interaction product of $Fe_2(MoO_4)_3$, $MoO_3$ and bismuth oxide for catalyzing oxidation of methanol to formaldehyde); 4,181,629 (supported catalyst of iron oxide and molybdenum oxide on silica, alumina and the like); 4,421,938 (a supported catalyst of at least two oxides of Mo, Ni, Fe and the like); and 5,217,936 (a catalyst of a monolithic, inert carrier and oxides of molybdenum, iron and the like).

In comparison to the silver catalyzed processes, iron-molybdate/molybdenum trioxide catalyzed processes produce higher yields of formaldehyde. Iron-molybdate, $Fe_2(MoO_4)_3$, in combination with molybdenum trioxide, $MoO_3$, constitute the metal oxide phases of exemplary commercially available metal oxide catalysts suitable for oxidizing methanol to formaldehyde. During the oxidation of methanol to formaldehyde, the $Fe_2(MoO_4)_3/MoO_3$ catalyst can be generated in situ from physical mixtures of pure molybdenum trioxide, $MoO_3$, and ferric oxide, $Fe_2O_3$. See co-pending application designated by U.S. Provisional Ser. No. 60/081,950 of Wachs, et al. Entitled "In Situ Formation of Metal Molybdate Catalysts," filed Apr. 15, 19098, incorporated herein by reference in its entirety. The molar ratio $MoO_3/Fe_2O_3$ of these catalysts may be varied. Typically, such catalysts used in industrial and commercial applications contain an excess of $MoO_3$. Thus, for example, the molar ratio $MoO_3/Fe_2O_3$ may vary from 1.5/1 to 12/1 or more. Excess $MoO_3$ is provided to ensure that sufficient amounts of $Fe_2(MoO_4)_3$ are formed in situ (from the mixture of $Fe_2O_3$ and $MoO_3$) for efficiently oxidizing methanol to formaldehyde in high yields.

Unfortunately, the use of excess $MoO_3$ in conjunction with $Fe_2O_3$ or other metal oxides and/or metal molybdates is problematic. Oxidizing methanol to formaldehyde using a metal molybdate/molybdenum trioxide type catalyst, e.g., $Fe_2(MoO_2O_4)_3/MoO_3$, is a highly exothermic process. The heat released during the oxidation reaction increases the catalyst and/or the fixed bed reactor temperature producing "hot spots" on the catalyst surface. These hot spots reach temperatures high enough to volatilize the $MoO_3$ species present within metal molybdate/molybdenum trioxide type catalysts. Thus, $MoO_3$ is sublimed from the hot spots so formed.

The sublimed $MoO_3$ species migrate downstream (e.g., within an exemplary fixed bed reactor housing the catalyst) towards cooler regions of the fixed bed reactor or the like. Typically, the downstream migration of sublimed $MoO_3$ species is facilitated by the incoming flow of the reactant gas feed stream containing, for example, methanol, air, and an optional inert carrier gas fed into the inlet end of a fixed bed reactor. The migrated $MoO_3$ species crystallize in the cooler downstream regions of the fixed bed reactor, for example, in the form of $MoO_3$ crystalline needles. Over time, the needle formation accumulates and ultimately obstructs the flow of the reactant gas feed stream through the fixed bed reactor. Thus, build up of $MoO_3$ crystals/needles in the downstream region causes a substantial pressure drop in the reactant gas feed stream flow rate as the reactant gas feed stream is directed downstream. This pressure drop impedes the efficient oxidation of methanol to formaldehyde. See, for example, U.S. Pat. Nos. 3,983,073 (col. 1, lines 35–52); and 4,024,074 (col. 1, lines 60–68); and U.K. Patent No. 1,463,174 (page 1, col. 2, lines 49–59) describing the aforementioned volatility problem. See also, "Fluidized bed improves formaldehyde process," C&EN, pp. 37–38 (Nov. 3, 1980; Popov, et al., "Study of an Iron-Molybdenum Oxide Catalyst for the Oxidation of Methanol to Formaldehyde," Institute of Catalysis, Siberian Branch of the Academy of Sciences of the USSR, Novosibinsk, Transcript from Kiretika & Kataliz, Vol. 17, No. 2, pp. 371–377, March–April, 1976; E. M. McCarron III, et al.; "Oxy-Methoxy Compounds of Molybdenum (VI) and their Relationship to the Selective Oxidation of Methanol Over Molybdate Catalysts, Polyhedron, Vol. 5, No. ½, pp. 129–139 (1986); and L. Cairati et al., "Oxidation of Methanol in a Fluidized Bed $Fe_2O_3$—$MoO_3$ Supported Silica," Chemistry and Uses of Molybdenum, Proceedings of the Fourth International Conference, CLIMAX MOLYBDENUM COMPANY, H. F. Baum and P. C. H. Mitchell, Editors, pp. 402–405, Aug. 9–13, 1982.

Often, the $MoO_3$ needle formation that occurs in the downstream region of the fixed bed reactor is so excessive that the reactor must be shut down, the needles cleaned out, and fresh catalyst charged therein. These steps unnecessarily increase the time, cost, inefficiency and/or complexity of operating a fixed bed reactor or the like for oxidizing methanol to formaldehyde.

The vanadia-titania ($V_2O_5$ supported by $TiO_2$) supported catalyst is a catalyst that can also selectively oxidize methanol to formaldehyde. Unfortunately, this catalyst has a disadvantage associated with its use. The vanadia-titania catalyst exhibits an extremely high catalytic activity. Due to this high catalytic activity, this catalyst continues to oxidize formaldehyde into carbon monoxide especially when a high concentration of formaldehyde is available. Consequently, the yield of formaldehyde is undesirably lowered.

Accordingly, there would be an advantage to provide a catalytic reactor bed arrangement and a process using the same that substantially alleviates, and/or eliminates the aforementioned crystallization problems associated with metal molybdate catalysts containing volatile $Mo/MoO_3$ species while simultaneously alleviating and/or eliminating the aforementioned undesirable continued oxidation of formaldehyde to carbon monoxide associated with vanadia-titania catalysts.

Further, (1) silver catalysts, (2) supported catalysts such as those containing silicon dioxide, non-sintered $Fe_2O_3$, bismuth interaction products, silica, and/or alumina, (3) catalysts containing zinc, zinc carbonates and/or indium, (4) shaped catalysts, and (5) the like are often prohibitively expensive to use. Accordingly, there remains a need for a catalytic bed reactor arrangement and a method using the same suitable for cost effectively oxidizing methanol to formaldehyde which minimizes the use of one or more of (1) silicon dioxide, (2) non-sintered $Fe_2O_3$, (3) interaction products of $Fe_2(MoO_4)_3$, and $MoO_3$, and bismuth, (4) silica, (5) alumina, (6) shaped catalysts for increasing mechanical strength, (7) catalysts containing $Zn(CO_3O_3)_2 \cdot 3Zn(OH)_2$, $In(NO_3)_3 \cdot 3H_2O$ or one or more of the compounds listed in U.S. Pat. No. 4,421,938, (8) a fibrous carrier material such as silica, or (9) the like.

SUMMARY OF THE INVENTION

It is therefore an object of the invention to provide a catalytic reactor bed arrangement of two or more catalysts, in a specified distribution, within one or more fixed bed reactors and a process using the same for converting methanol to formaldehyde that alleviates and/or eliminates the above-mentioned problems associated with the volatility of $MoO_3$ and the undesired continued oxidation of formaldehyde to carbon monoxide associated with vanadia-titania catalysts.

It has been surprisingly discovered that use of a substantially pure vanadia-titania catalyst (e.g., essentially free of volatile $MoO_3$ species) distributed in an upstream region of one or more fixed bed reactors together with a metal molybdena catalyst within the downstream region of the fixed bed reactor provides a high selectivity (e.g., nearly 90–100%) and a high conversion % (e.g., at least 85–95%) for oxidizing methanol to formaldehyde while eliminating and/or alleviating the above-mentioned volatility and continued oxidation problems.

According to one aspect of the invention, oxidation of methanol to formaldehyde is achieved by the exemplary process described below. The process comprises the steps of:

(a) introducing a reactant gas feed stream comprising methanol into an inlet end of a catalyst reaction zone having said inlet end, an upstream region, a downstream region, and an outlet end, wherein the catalyst reaction zone comprises a fixed bed reactor with a vanadia-titania first catalyst in the upstream region and a metal molybdate second catalyst in the downstream region, and wherein the upstream region is essentially free of a volatile $MoO_3$ species;

(b) contacting and oxidizing the methanol to formaldehyde with the vanadia-titania first catalyst to yield a partially oxidized reactant gas feed stream containing residual methanol; and (c) then contacting and oxidizing the residual methanol to formaldehyde with the metal molybdate second catalyst to yield a product gas stream.

According to another aspect of the invention, an exemplary catalytic reactor bed comprises a vanadia-titania catalyst in an upstream region and a metal molybdate catalyst in a downstream region of the fixed bed reactor, respectively. The vanadia-titania catalyst must be essentially free of a volatile species of $MoO_3$ sufficient to alleviate and/or eliminate a substantial pressure drop of the reactant gas feed stream (comprising methanol) as it flows through the fixed bed reactor. The metal molybdate catalyst must initially be essentially free of vanadia ($V_2O_5$) sufficient to alleviate and/or eliminate a substantial further oxidation of the formaldehyde such as to carbon monoxide.

DETAILED OF THE PREFERRED EMBODIMENTS

Oxidizing methanol to formaldehyde may be facilitated by the use of two or more catalysts having a specified distribution within a catalyst reaction zone. Typically, the catalyst reaction zone comprises a fixed bed reactor having an inlet end, an upstream region, a downstream region and an outlet end. Preferably, the inlet end, the upstream region, the downstream region and the outlet end are provided in the same order as indicated herein. For example, see FIGS. 2 and 3. The catalysts are distributed as described in greater detail below with reference to the exemplary fixed bed reactors depicted in FIGS. 2 and 3. These fixed bed reactors are suitable for carrying out the process of the invention including the exemplary process steps outlined in FIG. 1.

Figure 1:
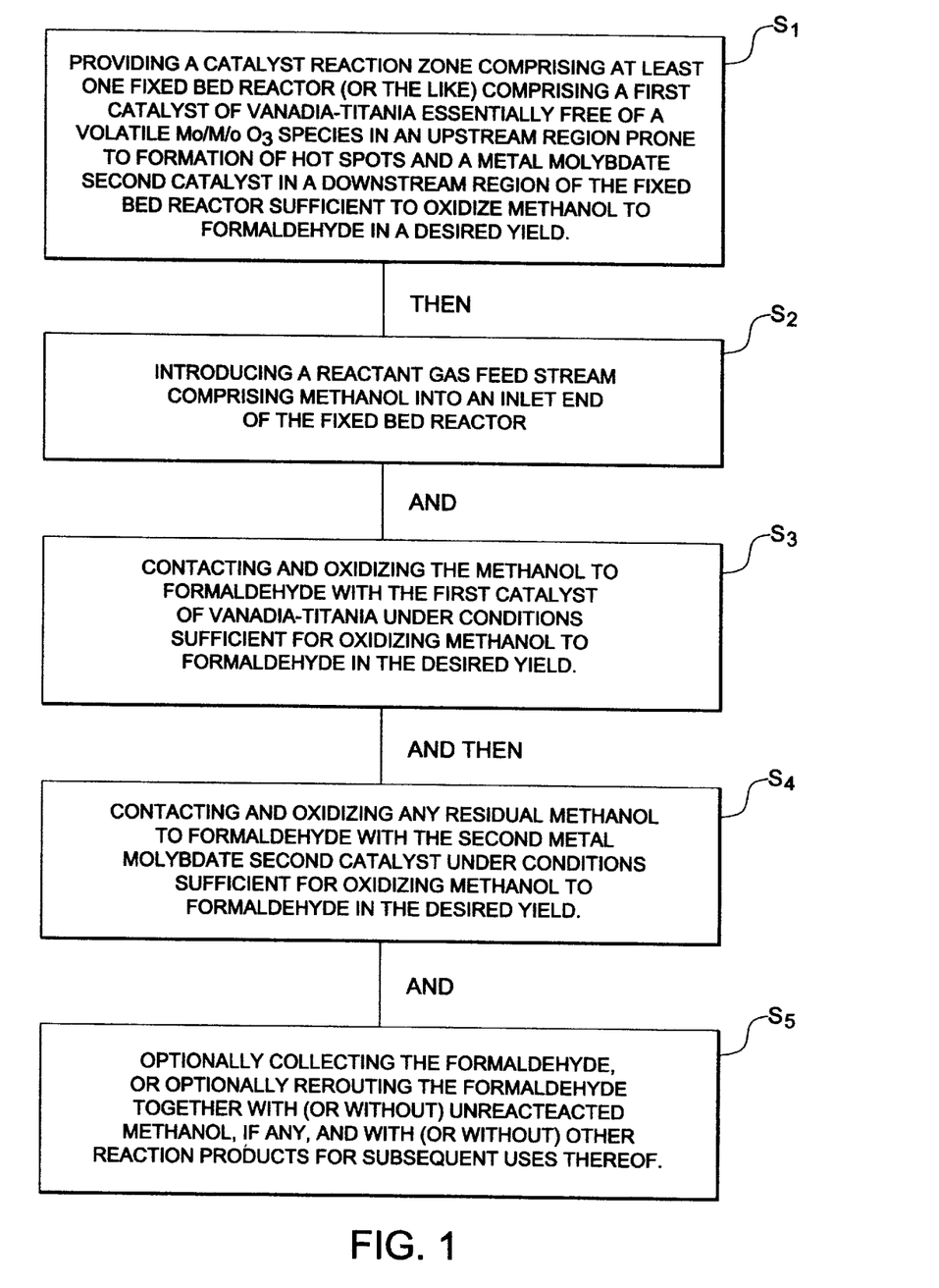
FIG. 1 is a flow chart depicting the process of this invention according to one embodiment.
Figure 2:
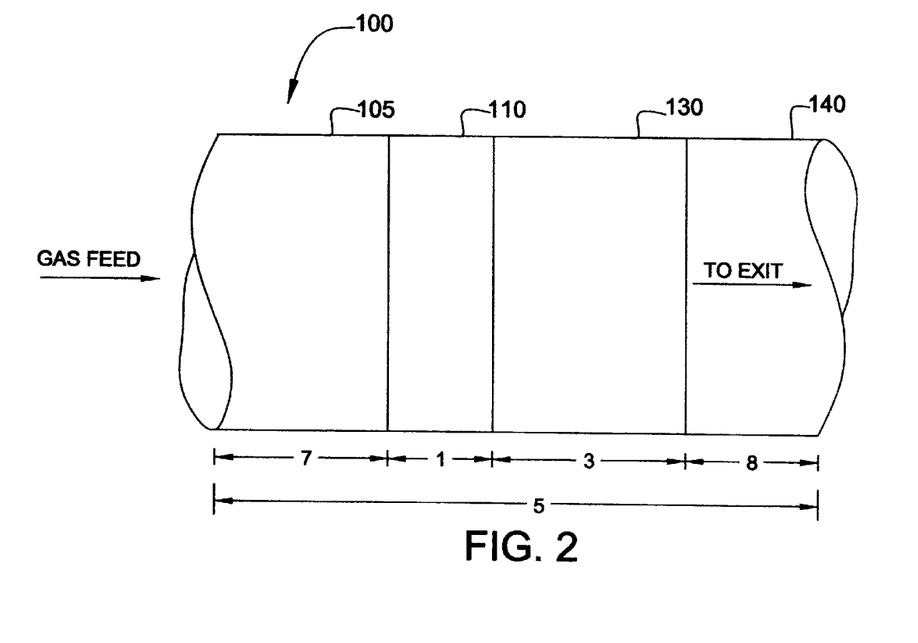
FIG. 2 is a schematic of a tubular fixed bed reactor according to one embodiment of the invention.
Figure 3:
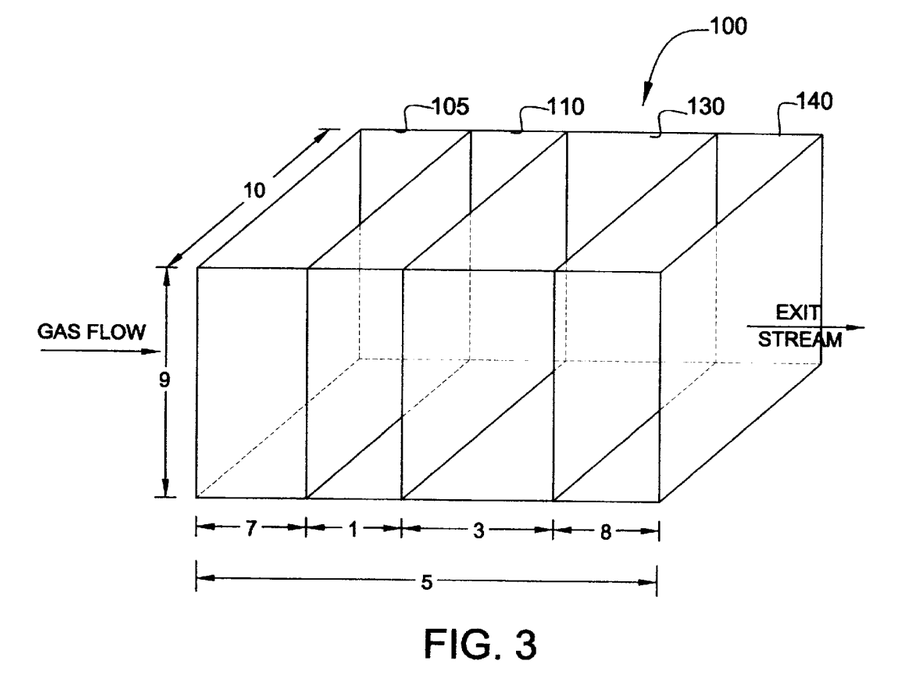
FIG. 3 is a schematic of a block fixed bed reactor according to another embodiment of the invention.

As used herein, the term "methanol" is intended to include pure methanol streams, paper (pulp) mill waste gas streams containing methanol, other waste gas streams containing methanol, methyl mercaptan and/or mixtures thereof Now referring to FIG. 1, process step $S_1$ comprises providing at least one fixed bed reactor (or the like). The fixed bed reactor includes a catalytic reactor bed (i.e., the upstream and downstream regions of the fixed bed reactor) comprising a plurality of catalysts in a specified distribution. The specified distribution comprises providing a vanadia-titania first catalyst (essentially free of a volatile $MoO_3$ species) in the upstream region of the fixed bed reactor and a metal molybdate second catalyst (initially, essentially free of $V_2O_5$ species) in the downstream region of the fixed bed reactor. For the reasons previously described, the upstream region of the fixed bed reactor is the region prone to substantial formation of hot spots during the catalytic oxidation of methanol to formaldehyde. With reference to FIGS. 2 and 3, typically, the upstream region 110 of depth 1 comprises from about ¼ to about ½ of the total depth 5 of the fixed bed reactor. Preferably, the upstream region comprises from about ¼ to about ⅜ of the total depth 5 of the fixed bed reactor, more preferably from about ⅓ to about ⅜ of the total depth 5 of the fixed bed reactor.

Further, with reference FIG. 1, process step $S_1$ comprises providing a metal molybdate second catalyst in the downstream region of the fixed bed reactor. The downstream region of the fixed bed reactor is substantially less prone to formation of hot spots than the upstream region because substantial conversion of methanol to formaldehyde (as described below) has already occurred in the upstream region of the fixed bed reactor. Accordingly, only residual methanol (yet unconverted to formaldehyde) is oxidized to formaldehyde in the downstream region. Typically, because the amount of the residual methanol is substantially less than the amount of the methanol in the reactant gas feed stream entering the upstream region, formation of hot spots is substantially suppressed in the downstream region. Accordingly, a conventional metal molybdate type catalyst (e.g., $Fe_2(MoO_4)_3$ together with excess $MoO_3$) may be and preferably is provided in the downstream region. As previously noted, because hot spot formation is suppressed in the downstream region, the volatility/crystallization/pressure drop problems associated with the use of volatile $MoO_3$ components in an upstream region are substantially attenuated or altogether avoided in the downstream region.

With reference to FIGS. 2 and 3, typically, the downstream region 130 of depth 3 comprises from about ½ to about ¾ of the total depth 5 of the fixed bed reactor. Preferably, the downstream region comprises from about ⅝ to about ¾ of the total depth 5 of the fixed bed reactor, more preferably from about ⅝ to about ⅔ of the total depth 5 of the fixed bed reactor.

The vanadia-titania first catalyst and the metal molybdate second catalyst provided in the specified distribution (e.g., step $S_1$ of FIG. 1) in a fixed bed reactor (e.g., in the catalyst reaction zone comprising one or more catalytic reactor beds having the upstream region and the downstream region) are provided in amounts, particle sizes, having surface areas and the like sufficient to oxidize an incoming reactant feed gas stream introduced into an inlet end (e.g., inlet end 105 of depth 7; see FIGS. 2 and 3) to yield a product gas stream at the outlet end (e.g., outlet end 140 of depth 8; see FIGS. 2 and 3) containing formaldehyde in a desired yield.

Referring now to step $S_2$ of FIG. 1, a reactant gas feed stream comprising methanol is introduced into an inlet end (e.g., inlet end 105 of depth 7; see FIGS. 2 and 3) of the fixed bed reactor. The depth 7 of the inlet end may be from about 1/1000 to about ½ the overall depth 5 of the fixed bed reactor. Alternatively, the inlet end 105 may not have any substantial or appreciable depth 7. In that case, inlet end 105 simply refers to an opening for receiving an incoming reactant gas feed stream. Typically, the reactant gas feed stream comprises methanol, air or excess oxygen, and optionally an inert carrier gas (e.g., $N_2$, He, Ar, or the like). The reactant gas feed stream enters the inlet end 105 and travels towards the outlet end 140.

As the reactant gas feed stream approaches the upstream region, the reactant gas feed stream encounters and comes in contact with the vanadia-titania first catalyst distributed in the upstream region 110 of the fixed bed reactor. Accordingly, (part of step $S_2$ of FIG. 1) contacting the reactant gas feed stream with the vanadia-titania first catalyst is accomplished. The flow rate of the incoming gas feed stream, its temperature, its humidity, and other parameters are adjusted to values suited to oxidizing methanol to formaldehyde. The details necessary to perform these adjustments are well known to those of ordinary skill in the art. However, some preferred operating parameters are provided in greater detail below.

The flow rate in terms of space velocity, where space velocity is measured in $sec^{-1}$ and defined as the sccm of gas flow per cc of catalyst volume, of the reactant gas feed stream fed into the inlet end of an exemplary fixed bed reactor ranges from about 0.1 $sec^{-1}$ to about 3.0 $sec^{-1}$ preferably ranges from about 0.3 $sec^{-1}$ to about 2.5 $sec^{-1}$, more preferably ranges from about 0.4 $sec^{-1}$ to about 2.2 $sec^{-1}$ and even more preferably ranges from about 0.5 $sec^{-1}$ to about 2.0 $sec^{-1}$. The reactor temperature in the upstream region of an exemplary fixed bed reactor typically ranges from about 250° C. to about 450° C., preferably ranges from about 325° C. to about 425° C., more preferably ranges from about 350° C. to about 400° C., and even more preferably ranges from about 360° C. to about 380° C. The gas stream has a first molar ratio of moles of methanol to moles of oxygen from about 5:19 to about 11:9.9, and preferably about 9.1:9.6. A second molar ratio of moles of methanol to moles of carrier gas is from about 5:74 to about 11:83, and preferably from about 9.1:83.

Upon passage of the reactant gas feed stream through the upstream region, a significant portion of the methanol content thereof is converted to formaldehyde. However, some residual (yet unoxidized) methanol will be present within the partially oxidized reactant gas feed stream. At this stage through the fixed bed reactor, the reactant gas feed stream typically also contains residual methanol, air, an inert carrier gas (if initially provided) and other oxidation products well known to those skilled in the art. However, because the upstream region of the fixed bed catalyst is essentially free of a volatile $MoO_3$ species, the highly exothermic nature of the methanol oxidation reaction yielding formaldehyde (in the upstream region) avoids the aforementioned volatility/sublimation/pressure drop problems associated with the presence of volatile $MoO_3$ species (i.e., in an upstream region prone to hot spot formation). As it passes through and exits the upstream region, the reactant gas feed stream is partially oxidized typically containing significant quantities of formaldehyde.

Upon exit from the upstream region 110, the partially oxidized reactant gas feed stream typically containing formaldehyde, and residual methanol (together with other components) encounters and comes in contact with the metal molybdate second catalyst provided in the downstream region 130 of depth 3. Therein, a conventional metal molybdate second catalyst is provided to oxidize the residual methanol (that may potentially be present in the partially oxidized reactant gas feed stream), thereby, potentially improving the formaldehyde yield.

The reactor temperature of the downstream region of an exemplary fixed bed reactor typically ranges from about 250° C. to about 450° C., preferably ranges from about 305° C. to about 425° C., more preferably ranges from about 310° C. to about 400° C., and even more preferably ranges from about 320° C. to about 350° C.

Typically, upon passage through the downstream region, the partially oxidized reactant feed gas stream is now essentially fully oxidized and the reactant gas feed stream is hereafter referred to as the product gas stream. Formaldehyde is a significant component of the product gas stream together with quantities of one or more of air, some unreacted methanol (if any), water vapor, an inert carrier gas (if any), oxygen, and other products such as DMM (dimethoxy methane), MF (methyl formate), DME (dimethyl ether), CO, $CO_2$ and the like, and any other reacted and unreacted materials as may be present in the feed stream.

As the reactant gas feed stream completes passage and oxidation through the upstream and downstream regions, process steps $S_3$ and $S_4$ (i.e., contacting with the vanadia-titania first and conventional iron-molybdate second catalysts and oxidizing methanol to formaldehyde; see FIG. 1) are essentially completed. The product gas stream then exits the outlet end 140 of depth 8. The outlet end 140 has a depth 8 which is from about 1/1000 to about 1/10 the overall depth 5 of the fixed bed reactor. Often, the outlet end 140 may not have any substantial or appreciable depth 8. In that case, outlet end 140 simply refers to an opening for releasing the product gas stream.

Optionally, thereafter, the product gas stream may be recycled into the inlet, the upstream region, or the downstream region as desired for further oxidation. However, if the product gas stream is to be recycled into the inlet or upstream region and possibly commingled with a fresh supply of an incoming reactant feed gas stream, it may be preferable (1) to first remove formaldehyde from the product gas stream by conventional means such as distillation, condensation or absorption and the like or (2) to substantially dilute the product gas stream to minimize the possible further oxidation of formaldehyde (in the upstream region) to its undesirable oxidation products such as CO, $CO_2$ or the Eke. Additionally, the product gas stream may be routed to another process that utilizes the product gas stream in its state as it exits the outlet end 140. Alternatively, the formaldehyde in the product gas stream may be collected by methods known to those of ordinary skill including distillation, condensation, absorption or the like.

The fixed bed reactors illustrated in FIGS. 2 and 3 have an inlet end 105 of depth 7, an upstream region 110 of depth 1, a downstream region 130 of depth 3, and an outlet end 140 of depth 8. Each of depths 1, 3, 7 and 8 may be adjusted to a value sufficient to facilitate oxidizing methanol to formaldehyde in the desired conversion and the desired selectivity.

Further, the exemplary fixed bed reactor of FIG. 2 has a diameter 11 and the fixed bed reactor of FIG. 3 has a height 9 and a width 10. Each of the dimensions corresponding to reference numerals 9, 10, and 11 may be adjusted upwards or downwards as necessary to accommodate the desired reactor size, the desired operating conditions, the desired conversion and selectivity.

As used herein, the term "selectivity" is determined by dividing the number of moles of formaldehyde formed by the number of moles of methanol consumed from the reactant gas feed stream times 100. Accordingly, selectivity is a percentage value. Selectivity indicates the percentage of formaldehyde formed as compared to the percentage of non-formaldehyde oxidation products of methanol such as CO, $CO_2$, DMM, MF, DME, etc. As used herein, the term "conversion" is determined by dividing the difference between the number of moles of methanol fed to the fixed bed reactor in the reactant gas feed stream minus the number of moles of methanol exiting the reactor by the total number of moles of methanol fed times 100. Accordingly, conversion is a percentage value. Conversion indicates the percentage of the moles of methanol that were oxidized to formaldehyde and any other non-formaldehyde oxidation products of methanol. Thus, if 2 moles of methanol are fed into the fixed bed reactor (e.g., in a reactant gas feed stream) yielding 1 mole of formaldehyde and 1 mole of methanol, then selectivity would equal 100% while conversion would equal 50%. Likewise, if 3 moles of methanol are fed into the fixed bed reactor (e.g., in a reactant gas feed stream) yielding 2 moles of formaldehyde and 1 mole of methanol, then selectivity would equal 100% while conversion would equal 66 and 2/3%.

Further, the fixed bed reactors are operated at an appropriate reactor temperature, a reactor pressure and a reactant gas feed stream flow rate sufficient for oxidizing methanol to formaldehyde in the desired yield, conversion and/or selectivity. Suitable exemplary reactor temperatures range from about 250° C. to about 450° C. Suitable exemplary reactor pressures range from about 7 psia (i.e., about ½ atm) to about 165 psia. Suitable exemplary reactant gas space velocities range from 0.1 $sec^{-1}$ to about 3.0 $sec^{-1}$. Other conditions suitable for oxidizing methanol to formaldehyde are used which are well known to those of ordinary skill in the art.

The vanadia-titania first catalyst, distributed in the upstream region of the reactor, suitable for use with this invention can be any of the known vanadia-titania catalysts with the proviso that the vanadia-titania catalyst is essentially free of $MoO_3$ (or any other volatile Mo species prone to sublimation at hot spots) in an amount sufficient to substantially impede the flow of methanol due to the aforementioned $MoO_3$ volatility problem. For example, the amount of $MoO_3$ should be no more than (a) 0.1%–3% (e.g., 1%) by weight based on the total weight of the vanadia-titania catalyst including any catalyst support or any other inert (or non-inert) material or (b) the moles of $V_2O_5$ of the vanadia-titania catalyst. Preferably, the vanadia-titania catalyst, distributed in the upstream region, is free of $MoO_3$ and/or other similar volatile metallic oxides that poison the catalyst bed. Vanadia-titania catalysts suitable for use in conjunction with this invention include, but are not limited to available vanadia-titania catalysts where the vanadia content is less than a monolayer.

Preferably, the vanadia is primarily provided as a metal oxide overlayer, with the oxide having a noncrystalline form. The supported vanadia catalysts useful in the process of this invention generally comprise a metal oxide substrate, such as titania ($TiO_2$), the surface of which is typically modified with a layer of an oxide of vanadium (e.g., deposited as a metal oxide overlayer). Further, the supported catalysts (e.g., $V_2O_5$ on $TiO_2$) behave differently than the unsupported bulk metal oxides (e.g., $V_2O_5$). Preferably, the vanadia overlaid on the titania support or substrate should be sufficient to attach to the titania surface in an amount which does not exhibit (or does not substantially exhibit) properties of bulk vanadia.

Preferably, at least about 25 wt. % of the vanadia coating will be in a noncrystalline form. Typically, if the vanadia loading on the titania support broadly ranges from about 0.1 wt. % to about 35 wt. % of the total catalyst weight then at least 25 wt. % will be in non-crystalline form, Further, titania may be employed, for example in the anatase and/or rutile forms. For example, at least about 25 wt. % (and generally from about 50 wt. % to about 100 wt. %) of the titania may be in the anatase form. The above-noted wt. % values are based on the total weight of the catalyst including the weight of the support substance. As recognized by those skilled in the art, the titania support material should be sufficiently free of impurities to prevent interference with the desired oxidizing catalytic activity. The titania may be prepared by any known conventional technique.

For example, the vanadia-titania catalysts of this invention may be prepared by impregnation techniques well-known in the art, such as incipient wetness, grafting, equilibrium adsorption, vapor deposition, thermal spreading, and the like. When using an incipient wetness impregnation technique, an aqueous or nonaqueous (e.g., organic) solution containing a vanadia precursor compound (together with an appropriate solvent thereof) is contacted with titani. The vanadia precursor (such as a salt) solution used may be aqueous or organic, with an amount of solvent sufficient to dissolve the precursor. Over time the vanadia precursor material is deposited onto the support, for example, by selective adsorption. Any excess solvent may be evaporated leaving behind the vanadia or its precursor or salt. Other impregnation techniques, such as vapor deposition and thermal spreading, do not require use of a solvent as does incipient wetness. These techniques may be desirable in some circumstances where, for example, volatile organic carbon (VOC) emissions are problematic. Alternatively, a suspension containing the metal oxide particles may be used to spread metal oxide particles on the substrate following the evaporation of the suspending vehicle at a temperature from about 100° C. to about 200° C. and calcination of the substrate and metal oxide particles at a temperature from about 400° C. to about 600° C. Further, the titania used in the catalyst of this invention may be composed of substantially porous particles of a diameter of from about 0.4 to about 0.7 micron. Preferably the titania support has a specific surface area of at least about 1 m$^2$/g (e.g., 9.5 m$^2$/g).

One way to disperse vanadia onto a titania support is to impregnate exemplary titania spheres or powders with a solution containing a vanadium compound. When impregnating a substrate with oxides, the vanadium is introduced, preferably by an aqueous solution, followed by drying and calcining. Criteria used to select the vanadium compounds include whether the compounds are soluble in the desired solvent and whether the compounds decompose at an acceptable rate at the calcination temperature to give the appropriate activated vanadium oxide. Illustrative of suitable compounds of vanadium for use in conjunction with this invention include, but are not limited to, vanadium halides, vanadium oxyacids, vanadium oxyacid salts, vanadium oxysalts, and/or other vanadium salts. Specific examples include vanadium tribromide, vanadium dichloride, vanadium trichloride, vanadium oxychoride, vanadium oxydichloride, vanadic acid, vanadyl sulfate, vanadium alkoxides, vanadium oxalate (which may be formed in situ by reaction of $V_2O_5$ with an aqueous solution of oxalic acid), and ammonium meta-vanadate.

The impregnation of the exemplary titania support (e.g., spheres, powders, or other shapes) with the vanadia precursor compound solution may be carried out, as noted above, in ways well known in the art using either wet or dry impregnation techniques. One convenient method is to place the titania particles into a rotary evaporator which is equipped with a steam jacket. An impregnating solution of a precursor compound which contains an amount of the desired metal to be included in the finished catalyst (as the metal) is added to the support particles and the mixture is cold rolled (no steam) for a time from about 10 to about 60 minutes. The cold rolling time should be sufficient to impregnate the support with the precursor compound solution. Water-soluble precursor compounds are generally preferred for industrial applications because of environmental concerns regarding VOC emissions. Nonetheless, when using an organic solvent, initial heating may be done in a nitrogen atmosphere to remove any flammable solvent. Next, steam is introduced and the solvent is evaporated. This usually takes from about 1 to about 4 hours. The impregnated support will normally be dried at temperatures ranging from about 50° C. to about 300° C. yielding a support with a vanadium overlayer thereon.

Eventually, the titania is removed from the rotary evaporator and calcined. The evaporation and calcination is conducted in a suitable oxidizing atmosphere such as air, other oxygen source gasses, etc. at a temperature typically from about 150° to about 800° C., and more preferably about from 400° to about 600° C., and even more preferably for about 1 to about 3 hours. The calcining is carried out over a period of time sufficient to covert the precursor compound to the corresponding vanadia. As recognized by those skilled in the art, calcining conditions need to be adjusted to avoid undesirably reducing the catalyst surface area or transforming the titania via solid state reactions. As is recognized by those skilled in the art, because some precursor compounds are air/moisture sensitive, they are prepared under a nitrogen atmosphere or the like. The time required to calcine the composite will, of course, depend on the temperature and, in general, may broadly range from about 0.5 to about 16 hours, though calcination times of less than about 7 hours may often be suitable. Calcination at about 450° C. for about 2 hours has proven to be suitable for adsorbing 1 wt. % (based on the final total catalyst weight) vanadia on the titania support. The precise time and temperature for calcination should be selected to avoid substantial crystal phase transformation of the preferred titanium anatase form into another crystalline form, such as rutile. The anatase form is preferred to the rutile form because the former exhibits greater surface area than the latter. As such, the former form exhibits greater catalytic activity in comparison to that of the latter rutile form.

The vanadia supported catalysts of this invention will typically have surface vanadia loadings from about 0.1 wt. % to about 35 wt. % (based on the total active catalyst weight), preferably from about 1 wt. % to about 20 wt. %, more preferably from about 1 wt. % to about 15 wt. %, and even more preferably from about 1 wt. % to about 10 wt. %.

Additional details relating to the preparation and structure of vanadia supported catalysts suitable for use in conjunction with the invention are well-known. For example, see Jehng et al., *Applied Catalysis A*, 83, 179–200, (1992); Jehng and Wachs, *Catalysis Today*, 16, 417–426, (1993); Kim and Wachs, *Journal of Catalysis*, 141, 419–429, (1993); Deo et al., *Applied Catalysis A*, 91, 2742, (1992); Deo and Wachs, *Journal of Catalysis*, 146, 323–334, (1994); Deo and Wachs, *Journal of Catalysis*, 146, 335–345, (1994); Jehng et al., *J. Chem. Soc. Faraday Trans.*, 91(5), 953–961, (1995); Kim et al., *Journal of Catalysis*, 146, 268–277, (1994); Banares et al., *Journal of Catalysis*, 150, 407–420, (1994) and Jehng and Wachs, *Catalyst Letters*, 13, 9–20, (1992).

Typically, the titania support used in accordance with the invention has a surface area in the range from about 1 m$^2$/g to about 150 m$^2$/g or more (e.g., 5–15 m$^2$/g). The titania may be used in any configuration, shape or size which exposes its surface and any vanadia layer dispersed thereon to the gaseous stream containing methanol passed in contact therewith. For example, titania can be employed in a particulate form or a deposited form. The deposited form includes, for example, titania (or vanadia on titania) deposited on a monolithic carrier or onto ceramic rings or pellets or the like. Typically, a vanadia on titania catalyst, is deposited on a ceramic or refractory inorganic carrier such as silicon carbide, silicon nitride, carborundum, steatite, alumina and the like. Rings or pellets are preferred. As particles, the titania, can be formed into various shapes, including but not limited to, pills, pellets, granules, rings, spheres and the like. Alternatively, use of free particulates (e.g., unshaped titania) may be desirable when large catalyst volumes are needed. Additionally, the active catalyst will be applied to the inert ceramic support in an amount to provide, for example, from about 1 wt. % to about 20 wt. % by weight, and preferably from about 5 wt. % to about 15 wt. %, based on the total weight of the catalyst including the support substrate and any carrier thereof Because the downstream region 130 is not as prone to formation of hot spots as is the upstream region 120, it is preferable and less expensive to use a conventional metal molybdate catalyst in the downstream region 130. Examples of metal molybdate catalysts suitable for use with the invention include, but are not limited to $Fe_2(MoO_4)_3$ and $Fe_2(MoO_4)_3/MoO_3$, other group VIII metal molybdate catalysts (e.g., molybdates of Fe, Co, Ni, Cr, Al, Zr, Zn, Mn, or mixtures thereof). The group VIII metal molybdate catalysts may contain $Mo/MoO_3$ in minor or larger quantities. Preferably, the metal molybdate catalyst is a metal molybdate/molybdenum trioxide catalyst such as $Fe_2(MoO_4)_3/MoO_3$. The $Fe_2(MoO_4)_3/MoO_3$ catalyst is preferably formed in situ during the oxidation of methanol to formaldehyde from a mixture of substantially pure $Fe_2O_3$ and $MoO_3$ wherein an excess of $MoO_3$ is typically provided. See co-pending application designated by U.S. Provisional Ser. No. 60/081,950 of Wachs et al. entitled "In Situ Formation of Metal Molybdate Catalysts," filed Apr. 15, 1998.

The metal molybdate second catalyst typically has a surface area ranging from about 0.1 $m^2/g$ to about 20 $m^2/g$ or more, usually ranging from about 2 $m^2/g$ to about 15 $m^2/g$, more preferably ranging from about 4 $m^2/g$ to about 14 $m^2/g$, and even more preferably ranging from about 4 $m^2/g$ to about 12 $m^2/g$.

Having described the invention, the following illustrative examples are provided. These examples are illustrative of preferred aspects of the invention and are not intended to limit the scope of the invention. All patents, publications and any other references cited herein are incorporated by reference herein in their entirety, respectively. In that regard, related provisional applications (1) "Dual Catalyst Bed Reactor for Methanol Oxidation" designated by Attorney Docket No. 00242.84298 filed on even date and (2) "Metal Molybdate/Iron-Molybdate Dual Catalyst Bed System and Process Using the Same for Methanol Oxidation to Formaldehyde" designated Attorney Docket No. 00242.84299 filed on even date are incorporated herein by reference in their entirety.

EXAMPLE 1

The oxidation of methanol over the catalyst distribution of the claimed invention was examined in a fixed-bed reactor: 1" outer diameter, 14 Birmingham Wire Gauge, 5' length steel tube and catalyst fillage is 18–48" (e.g., 36": the sum of 24" of Perstorp KH-44 Fe—Mo in the downstream region with 12" of $V_2O_5/TiO_2$ in the upstream region) with 0"–24" inert rings (e.g., inert ceramic rings from Perstorp Polyols, Inc. of Toledo, Ohio) on the bottom (i.e., between the catalyst bed and the outlet end) and 0"–24" inert rings on the top (i.e., between the inlet end and the catalyst bed).

Each catalytic test consisted of a gas stream of $CH_3OH/O_2/He$ with a methanol feed concentration of 9.1% and a total flow rate of 28.3 slpm (standard liters per minute). Methanol, oxygen, and nitrogen were present in a molar ratio of 9.1/9.6/81.3.

In order to examine the full effect of temperature on methanol oxidation, the reactor temperature was varied from about 260° C. to about 300° C. under recycle conditions. The reaction products were analyzed with a gas chromatograph: MTI Q30H with one 14 meter OV-1 column, one 8 meter Stabilwax column and one 10 meter Molsieve 5A column obtained from MTI of Fremont, Calif. The test results for a catalyst bed with 12" of $V_2O_5/TiO_2$ in the upstream region followed by 24" of Perstorp KH-44 Fe—Mo in the downstream region are presented in Table 1 below.

The catalyst of the claimed invention yielded about a 97% conversion and a selectivity (formaldehyde) of 87% at 290° C. in the laboratory.

TABLE 1

Methanol Conversion and Product Selectivity

| T(° C.) | Conversion (%) | Selectivity (%) | | | | | |
|---|---|---|---|---|---|---|---|
| | | HCHO | DME | MF | DMM | CO | $CO_2$ |
| 260 | 92.7 | 90.7 | 0.75 | 0.07 | 0 | 6.83 | 0.07 |
| 270 | 94.8 | 90.6 | 0.45 | 0.03 | 0 | 7.63 | 0.16 |
| 275 | 95.7 | 87.5 | 0.35 | 0.03 | 0 | 11.05 | 0.18 |
| 280 | 95.6 | 88.1 | 0.33 | 0.05 | 0 | 10.48 | 0.22 |
| 280 | 96.5 | 84.0 | 0.12 | 0.02 | 0 | 14.93 | 0.28 |
| 290 | 97.1 | 86.6 | 0.21 | 0.02 | 0 | 12.42 | 0.21 |
| 300 | 98.0 | 78.7 | 0.07 | 0.02 | 0 | 20.50 | 0.30 |

HCHO indicates the selectivity for formaldehyde. Likewise, DME, MF, and DMM indicate the selectivity for dimethyl ether, methyl formate, and dimethoxy methane, respectively.

EXAMPLE 2

Instead of the reactor indicated in EXAMPLE 1 above, one may use the following reactor which is a self-contained formaldehyde manufacturing laboratory:

1. Liquid methanol storage, metering and vaporization equipment.
2. Process gas compression and metering equipment.
3. A reactor unit comprised of:
    a. A one inch OD, 60 inch long, 14 BWG, carbon steel tube surrounded by:
        1) A circulating, temperature controlled, bath of a heat transfer oil with an atmospheric boiling point of 257° C.
        2) A vapor pressure measurement and control system for the heat transfer oil.
        3) A stainless steel tube thermowell of diameter of 0.125 inch extending axially for the length of the tube, containing a wire thermocouple capable of being positioned at any point within the length of the thermowell.
4. A catalyst bed installed in the reactor tube void space of 0.834 inch diameter, which may vary in depth from essentially zero inch to 48 inches and may be comprised of one or more subdivisions of catalyst types, mixtures, or inert materials.
5. Formaldehyde separation equipment commonly known as an "Absorber" comprised of four sections of packing and the required handling equipment for circulation and cooling.
6. Piping and equipment necessary for operation of the catalyst bed in a recycle mode so as to allow the oxygen level of the process gas to be controlled at less than atmospheric levels.

7. Oxygen measuring and control equipment for maintaining precise control of oxygen in the catalyst bed.

8. Instrumentation and equipment to control the process gas pressure during the formaldehyde manufacturing process.

The above-identified reactor may be used with a catalyst bed having 12" of $V_2O_5/TiO_2$ in the upstream region followed by 24" of Perstorp KH-44 Fe—Mo in the downstream region thereof It will be understood that the claims below are intended to cover all changes and modifications of the examples and preferred embodiments of the invention herein chosen for the purpose of illustration which do not constitute departures from the spirit and scope of the invention.

We claim:

1. A process for oxidizing methanol to formaldehyde in a catalyst reaction zone comprising a fixed bed reactor having an inlet end, a depth, a width, a length, an upstream region, a downstream region, and an outlet end, said process comprising the steps of:

(a) introducing a reactant gas feed stream into said inlet end, wherein said reactant gas feed stream comprises methanol; and (b) flowing said reactant gas feed stream through said upstream region and oxidizing said methanol to said formaldehyde to yield a partially oxidized reactant gas feed stream containing formaldehyde and potentially unoxidized residual methanol;

(c) and then flowing said partially oxidized reactant gas feed stream through said downstream region and oxidizing said residual methanol to formaldehyde to yield a product gas stream, wherein a vanadia-titania first catalyst suitable for oxidizing said methanol to said formaldehyde is distributed in said upstream region, wherein said vanadia-titania first catalyst is substantially free of volatile $MoO_3$, and wherein a metal molybdate second catalyst suitable for oxidizing any of said residual methanol to said formaldehyde is distributed in said downstream region.

2. The process of claim 1, wherein said metal molybdate second catalyst further comprises excess $MoO_3$.

3. The process of claim 1 further comprising selecting said metal molybdate second catalyst from the group consisting of $Fe_2(MoO_4)_3/MoO_3$, $CoMoO_4/MoO_3$, $NiMoO_4/MoO_3$, $Al_2(MoO_4)_3/MoO_3$, $Zr(MoO_4)_3/MoO_3$ and mixtures thereof.

4. The process of claim 3, wherein said metal molybdate second catalyst is formed in situ from mixtures of $MoO_3$ and group VIII metal oxides.

5. The process of claim 1, wherein said flow rate of said reactant gas feed stream is sufficient to produce a space velocity of at least 0.1 $sec^{-1}$ for said reactant gas feed stream.

6. The process of claim 1, wherein said formaldehyde in said product gas stream has a conversion of at least 85% and a selectivity of at least 90%.

7. The process of claim 1, wherein said upstream region comprises from about one-fourth to about one-half of said depth of said fixed bed reactor nearest said inlet end of said fixed bed reactor, and said downstream region of said fixed bed reactor comprises from about one-half to about three-fourths of said depth of said fixed bed reactor nearest said outlet end of said fixed bed reactor.

8. The process of claim 1, wherein said upstream region comprises from about one-third to about one-half of said depth of said fixed bed reactor nearest said inlet end of said fixed bed reactor, and downstream region of said fixed bed reactor comprises from about one-half to about two-thirds of said depth of said fixed bed reactor nearest said outlet end of said fixed bed reactor.

9. The process of claim 1, wherein said reactant gas feed stream comprises methanol, air and an optional inert carrier gas.

10. The process of claim 9, wherein said inert carrier gas is selected from the group consisting of $N_2$, He, Ar, and mixtures thereof.

11. The process of claim 1, wherein said upstream region is maintained at an upstream reactor temperature range from about 250° C. to about 450° C. and said downstream region is maintained at a downstream reactor temperature from about 250° C. to about 450° C.

12. The process of claim 1, wherein said reactor is operated at a reactor pressure from about 7 psia to about 165 psia.

13. The process of claim 1, wherein said metal molybdate second catalyst is formed in situ from NiO and $MoO_3$.

14. The process of claim 1, wherein said metal molybdate second catalyst is formed in situ from $Fe_2O_3$ and $MoO_3$.

15. The process of claim 1, wherein said methanol is a pulp mill waste stream or other process waste stream comprising methanol and optionally comprising methyl mercaptan.

16. The process of claim 15, wherein said pulp mill waste stream comprises at least about 20% methanol and said reactor is operated at a temperature to oxidize said methanol to said formaldehyde at a conversion of at least about 5%.

17. The process of claim 16, wherein said methanol is oxidized to said formaldehyde at a selectivity of at least about 60%.

18. The process of claim 17, wherein said selectivity is at least about 75%.

19. The process of claim 1, wherein said methanol is oxidized to said formaldehyde at a conversion of at least about 97% and said gas stream consists essentially of methanol, oxygen, and a carrier gas.

20. The process of claim 19, wherein said methanol is oxidized to said formaldehyde at a selectivity of at least about 78%.

21. The process of claim 20, wherein said selectivity is at least about 87%.

22. The process of claim 1, wherein step (a) further comprises mixing said product stream with said gas stream.

23. The process of claim 1, wherein step (b) further comprises mixing said product stream with said gas stream.

24. The process of claim 1, wherein step (c) further comprises mixing said product stream with said gas stream.

* * * * *

UNITED STATES PATENT AND TRADEMARK OFFICE
CERTIFICATE OF CORRECTION

| | | |
|---|---|---|
| PATENT NO. | : 6,552,233 B2 | Page 1 of 1 |
| DATED | : April 22, 2003 | |
| INVENTOR(S) | : Israel E. Wachs et al. | |

It is certified that error appears in the above-identified patent and that said Letters Patent is hereby corrected as shown below:

Title page,
Item [73], Assignees, "Resings" has been replaced with -- Resins --.

Signed and Sealed this

Twenty-first Day of October, 2003

JAMES E. ROGAN
*Director of the United States Patent and Trademark Office*